United States Patent [19]

Mora

[11] Patent Number: 4,575,496
[45] Date of Patent: Mar. 11, 1986

[54] ERYTHROMYCIN SALT OF THE O-CARBONYL(1-THIAZOLIDINYL)-BENZOIC ACID AND PHARMACEUTICAL COMPOSITIONS CONTAINING IT

[75] Inventor: Camillo C. Mora, Piacenza, Italy

[73] Assignee: Camillo Corvi S.p.A., Italy

[21] Appl. No.: 561,529

[22] Filed: Dec. 15, 1983

[30] Foreign Application Priority Data

Feb. 16, 1983 [IT] Italy .................. 19621 A/83

[51] Int. Cl.⁴ .................. A61K 31/71; C07H 17/08
[52] U.S. Cl. .................. 514/29; 536/7.2
[58] Field of Search .................. 536/7.2, 7.1; 424/180; 514/29

[56] References Cited

U.S. PATENT DOCUMENTS 4,264,765 4/1981 Bodor et al. .................. 536/7.2
4,396,613 8/1983 Kirst .................. 536/7.1

Primary Examiner—Johnnie R. Brown
Assistant Examiner—Elli Peselev
Attorney, Agent, or Firm—Ostrolenk, Faber, Gerb & Soffen

[57] ABSTRACT

The present invention concerns the new erythromycin salt of the o-carbonyl(1-thiazolidinyl)-benzoic acid having the formula

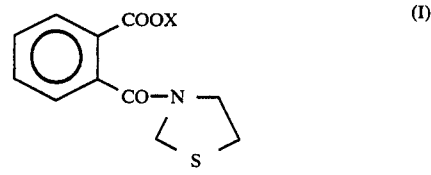

wherein X represents the monovalent cation of erythromycin. The new salt constitutes a novel antibiotic complex for the selective therapy of the respiratory tract.

10 Claims, No Drawings

ERYTHROMYCIN SALT OF THE O-CARBONYL(1-THIAZOLIDINYL)-BENZOIC ACID AND PHARMACEUTICAL COMPOSITIONS CONTAINING IT

DESCRIPTION

The instant invention concerns the erythromycin salt of o-carbonyl(1-thiazolidinyl)-benzoic acid.

Moreover, the present invention concerns a process for making said erythromycin salt.

The present invention also concerns pharmaceutical compositions, which are particularly useful for the selective therapy of the respiratory tract in human and veterinary medicine, said pharmaceutical compositions having mucolytic, fluidifying activity (viz. they increase the amount of and liquefy bronchial secretions).

The erythromycin salt of the present invention clearly differs, as for its chemical constitution, from all the other salts made heretofore in as much as the erythromycin base (either in its anhydrous or hydrate form) is salified with a new acid, viz. o-carbonyl(1-thiazolidinyl)-benzoic acid or flubetizinic acid, which is the subject matter of BE 892,516 of the applicant.

Said acid explicates a mucolytic, fluidifying pharmacological activity on the broncho-pulmonary secretions which is particularly compatible with the antibiotic activity of erythromycin.

Therefore, the inventive salt constitutes a new antibiotic complex suitable for the selective therapy of the respiratory tract.

Erythromycin, as known, is an antibiotic substance suitable for curing gram-positive infections and it is particularly effective against staphylococci, streptococci and pneumococci even when these are resistant to the other antibiotic drugs. Erythomycin is also effective for curing infections caused by mixtures of gram-positive and gram-negative bacteria.

The compound having the hereunder shown chemical formula (II) has the following main physico-chemical characteristics:

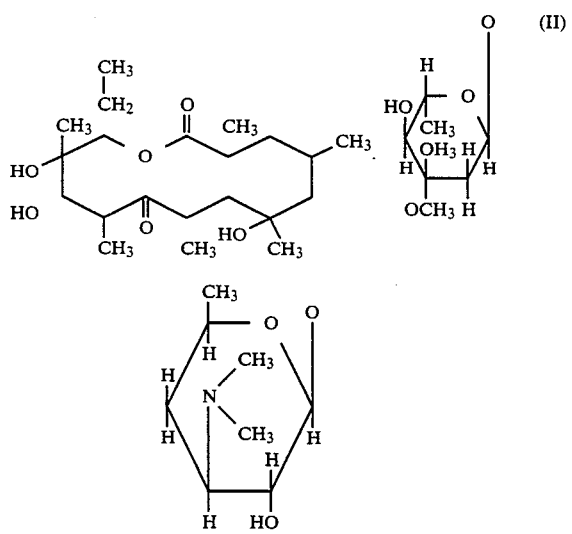

Empirical formula: $C_{37}H_{67}NO_{13}$
M.W. 733.92-Crystallizes with 2 mol.$H_2O$, mp 135°-140° C. (dried at 56° C. and 8 mm).
Solubility in water: 2 mg/ml.

The salt of the present invention derives from the combination of the erythromycin base of formula (II) with the 2-(1,3-thiazolidin-3-yl)-benzoic acid (CO/11-77a) of formula (III)

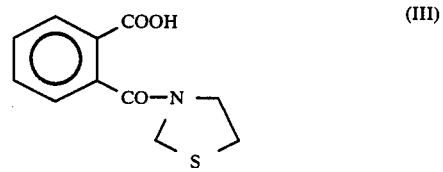

More particularly, the inventive salt can be obtained by reacting equimolar amounts (or, possibly, as it is known to the skilled artisans, with a slight excess of one of the two reactants) of erythromycin base and of flubetizinic acid, either in water or alcohol, preferably in ethanol. The reaction proceeds within a relatively wide range of temperatures and time, depending on whether water or alcohol is used as the solvent. Normally, using water and operating at a temperature of from 15° C. to 30° C., the reaction is completed in about 20–26 hours; whereas when using alcohol, it takes approximately 40–60 minutes for completion.

The inventive salt, identified by applicants with the code CO/1316, has the following physico-chemical characteristics:

Empirical formula: $C_{48}H_{78}O_{16}N_2S$
M.W. 971.224
Solubility: in water at ambient temperature 3% W/V;
in methanol=57%; in chloroform=50%; in acetone=50%;
in ethanol=50%; in 95% ethanol=32%; in dioxane=15%;
in toluene=0.3%; in ethyl ether=0.1%; in n-hexane=pratically insoluble.

Structural identification:

I.R. ($cm^{-1}$, mineral oil) 3400, wide band ($\gamma OH$); 1735 ($\gamma_{CO}$ cyclic lactone); 1695 ($\gamma_{CO}$ ketone); 1620, wide band ($\gamma_{as}$ COO$^-$ and $\gamma_{CO}$ amide; 1585 and 1560 ($\gamma_{C=C}$ arom.); 1170 and 1080.

NMR ($\delta$ppm tetramethylsilane, solvent: $CDCl_3$): 8.2÷8.05 complex absorption and 7.65÷7.20 complex absorption (1H and 3H; arom.hydrogens) 3.3 singlett (3H, $CO_3O$); 2.67 singlett [6H, $(CH_3)_2$, $NH^{\oplus}$]; 1.51+1 (overall absorption due to $10CH_3$).

The stoichiometric ratio of the salt components is checked by evaluating the integrals relating to the aromatic protone at 8.20÷8.05 $\delta$ppm (relating to the flubetizinic acid) and the singlet at 2.67 (relating to the salified erythromycin).

The inventive salt is prepared according to methods known in the art, i.e. by reacting the erythromycin, hydrated in water, with the flubetizinic acid and carrying out the salt formation by slowly transforming the base into the salt, or by dissolving the two salt components in absolute ethanol and evaporating to dryness and, finally, dissolving the so obtained salts in $H_2O$ solvent, recovering the anhydrous salts by crystallization.

In order to better illustrate the inventive preparation the following non-limiting examples are given.

EXAMPLE 1

15.4 g of finely subdivided dihydrated erythromycin base (M.W. 770) is suspended in 200 ml distilled water with 4.7 g flubetizinic acid (M.W. 237.28) in a 300 ml flask provided with magnetic stirrer. The reaction mixture is left 24 hours at ambient temperature, under stirring. A change in the form of the suspension is noticed, which, at the end, constitutes a white, silky precipitate. It is filtered using a Buchner funnel and dessicated at 56° C. and at a pressure of 10 mm Hg. The yield is 16.3 g of dry product which corresponds to approx. an 84% yield.

The formed salt has a mp=120°-125° C.

EXAMPLE 2

The same quantity of reagents as shown in example 1 is put on a rotating dryer of the capacity of 500 ml, with the addition of 150 ml absolute ethanol; the reaction mixture is dissolved at 50° C. and then the formed salt is evaporated to dryness. The so obtained crude salt which weighs approximately 16.9 g is crystallized from water, filtered on a Buchner and dessicated as outlined in example 1.

The yield of the pure salt corresponds to that obtained in example 1.

The erythromycin salt of the present invention is suitable for the therapy of broncho-pulmonary diseases characterized by infections deriving from bacteria which require the antibiotic therapy, as well as by catarrhal conditions which require a mucolytic fluidifying therapy. Both the therapies are explicated by the novel antibiotic product of the present invention.

The compositions of the present invention are generally presented for oral administration such as coated tablets or capsules, they are also presented for rectal administration as suppositories.

Examples of suitable vehicles or carriers for making coated tablets and capsules are: starch, lactose, aerosil, magnesium stearate and talc; whereas for preparing suppositories a mass made of saturated fatty acids triglycerides is used.

In human therapy, the salt of the present invention can be administered in a daily dosage of from 250 to 1500 mg. The exact dose depends upn the age, body weight, the conditions of the patient, and on the frequency and mode of administration. Normally, for an adult, oral doses are from 250 to 500 mg. 2 or 3 times per day, or via the rectal route, 250 mg doses, 1-3 times per day.

The bio-pharmacological data is reported in the folliwng Tables which show: (Table 1) the values of the antibiotic activity on 11 meaningful strains, comparing the pure antibiotic with the novel salt, in vitro; (Table 2) the activity of the salt CO/1316 against staphylococcus aureus (oral therapy); (Table 3) the activity of the salt CO/1316 against the staphylococcus aureus (intramuscular therapy). In Table 4, the activity data relating to the mucus production in the rabbit is reported, according to the method by Scuri et al., published in Boll. Chim.Farm.119, p.181, 1980. Finally, in Table 5 is shown the acute oral toxicity of the salt which substantially coincides with that of the erythromycin base.

TABLE 1

Antimicrobic activity, in vitro.

| Tested strains | $CIM^{(1)}$ values (mcg/ml) | |
|---|---|---|
| | Erythromycin | CO/1316 (erythromycin-flubetizinate) |
| Staph. aureus 1414[3] | 10 | 10 |
| Staph. aureus 6538[3] | 10 | 10 |

TABLE 1-continued

Antimicrobic activity, in vitro.

| Tested strains | $CIM^{(1)}$ values (mcg/ml) | |
|---|---|---|
| | Erythromycin | CO/1316 (erythromycin-flubetizinate) |
| Staph. epiderm. clin.[2] | 10 | 10 |
| Staph. epiderm. clin.[2] | 0.1 | 0.1 |
| Micrococcus luteus 9341[3] | 0.1 | 0.1 |
| Strept. faecalis 8043[3] | 0.3 | 0.6 |
| Pseudomonas aeruginosa | +100 | +100 |
| Escherichia coli 418 | 25 | 50 |
| Serr. marcescens cl.[2] | 50 | 100 |
| Proteus vulgaris | 2.5 | 5 |
| Candida albicans | 100 | 100 |

[1]CIM = Mic = Minimal inhibitory concentration
[2]Clin. = Isolated clinically.
[3]The 4-digit strains are ATCC's

TABLE 2

Activity of the salt CO/1316 (erythromycin flubetizinate) against the staphylococcus aureus experimental infections. Oral administration.

| Infecting organism | Rating of infection | Drug | N° of treatments | $DI_{50}$ | Confidence limits (P = 0.05) |
|---|---|---|---|---|---|
| Staphylococcus aureus | serious | CO/1316 | 1 | 560 | 1736-180 |
| | | | 1 | 720 | 1944-267 |
| | medium | CO/1316 | 1 | 350 | 1015-121 |
| | | | 1 | 510 | 1410-355 |
| | serious | CO/1316 | 5 | 180 | 340-95 |
| | | | 5 | 410 | 902-186 |
| | medium | CO/1316 | 5 | 84 | 261-28 |
| | | | 5 | 170 | 297-97 |

TABLE 3

Activity of the salt CO/1316 (erythromycin flubetizinate) against staphylococcus aureus infections. Intramuscular treatment.

| Infecting organism | Rating of infection | Drug | N° of treatments | $DI_{50}$ | Confidence limits (P = 0.05) |
|---|---|---|---|---|---|
| Staphylococcus aureus | serious | CO/1316 | 1 | 210 | 588-75 |
| | | | 1 | 390 | 1014-150 |
| | medium | CO/1316 | 1 | 98 | 176.4-54.4 |
| | | | 1 | 270 | 391-135 |
| | serious | CO/1316 | 5 | 110 | 308-39 |
| | | | 5 | 260 | 972-118 |
| | medium | CO/1316 | 5 | 76 | 129-45 |
| | | | 5 | 152 | 273-84 |

TABLE 4

Activity on the rabbit mucoproduction.

| Substance | Dose mg/kg | Mucoproduction: Var. % | Anim. with increase Treated anim. | % |
|---|---|---|---|---|
| CO/1316 | 40 ev | +45 | 9/14 | 64/2 |
| Erythromycin | 30 ev | Inactive | 0/10 | — |

TABLE 5

Oral acute toxicity in the rat

| Erythromycin base: | $DL_{50} > 5.0$ g/kg |
|---|---|
| CO/1316: | $DL_{50} > 5.0$ g/kg |

I claim:

1. The erythromycin salt of 2-(1,3-thiazolidin-3-yl)-benzoic acid in which the salt is formed at the nitrogen moiety of said erythromycin.

2. A pharmaceutical composition having mucolytic, fluidizing activity on the broncho-pulmonar secretions containing, as the active substance, a pharmacologically effective amount of the salt of claim 1 and a pharmaceutical vehicle.

3. A pharmaceutical composition in unit dosage form useful for the therapy of gram-positive and of mixed gram-positive and gram-negative bacterial infections, containing as the active substance 250-500 mg of the salt of claim 1 in combination with a pharmaceutical vehicle.

4. A method of treating a bacterial infection comprising administering to a host having a bacterial infection a pharmacologically effective amount of the salt of claim 1.

5. A method according to claim 4 in which the amount administered is from 250-1500 mg per day.

6. A method according to claim 4 in which the administration is oral.

7. A method according to claim 6 in which the amount administered is 250-500 mg, 2-3 times per day.

8. A method according to claim 4 in which the administration is rectal.

9. A method according to claim 8 in which the amount administered is 250 mg, 1-3 times per day.

10. A pharmaceutical composition having anti-bacterial activity containing, as the active substance, a pharmacologically effective amount of the salt of claim 1 and a pharamceutical vehicle.

* * * * *